United States Patent [19]

Stöl et al.

[11] 4,427,808
[45] Jan. 24, 1984

[54] COMPOSITE POLYMERIC MATERIAL FOR BIOLOGICAL AND MEDICAL APPLICATIONS AND THE METHOD FOR ITS PREPARATION

[75] Inventors: Miroslav Stöl; Miroslav Tolar; Milan Adam; Pavel Čefelin; Jaroslav Kálal, all of Prague, Czechoslovakia

[73] Assignee: Ceskoslovenska akademie ved, Prague, Czechoslovakia

[21] Appl. No.: 283,424

[22] Filed: Jul. 15, 1981

[30] Foreign Application Priority Data

Jul. 21, 1980 [CS] Czechoslovakia .................. 5125-80

[51] Int. Cl.$^3$ .............. C07G 7/00; C08L 89/06; G02C 7/04
[52] U.S. Cl. .................................... 524/24; 523/105; 523/106; 524/498; 524/845; 525/54.1; 525/937; 351/160 H; 260/123.7
[58] Field of Search ............... 523/105, 106, 113, 114; 524/21, 24, 498, 460, 845; 525/54.1, 937; 351/160 H; 260/123.7

[56] References Cited

U.S. PATENT DOCUMENTS 4,264,155  4/1981  Miyata ............................. 524/498
4,388,428  6/1983  Kuzma et al. ...................... 523/106

OTHER PUBLICATIONS

The Condensed Chemical Dictionary, Eighth Edition, Van Nostrand Reinhold Co., New York, 1971, pp. 459, 589.
Hackh's Chemical Dictionary, Fourth Edition, McGraw-Hill Book Co., New York, 1972, pp. 432 & 624.

*Primary Examiner*—John Kight, III
*Assistant Examiner*—Nathan M. Nutter
*Attorney, Agent, or Firm*—Murray Schaffer

[57] ABSTRACT

The invention relates to a composite polymeric material suitable for biological and medical applications and to the method for preparation thereof. The composite material consists of 1–99 wt. % of hydrophilic polymer or copolymer based on methacrylic or acrylic esters, 1–99 wt. % of fibrillar collagen, and up to 2.5 wt. % of a crosslinking agent, based on both polymeric components. The composite material may further comprise biologically active compounds and other auxiliary materials, as fillers and/or plasticizers. The composite material is prepared by dispersing the fibrillar collagen in a solution or a highly swollen dispersion of the synthetic hydrophilic polymer or copolymer in a lyotropic agent and the subsequent removal of the lyotropic agent, thus forming a matrix of the synthetic polymer or copolymer penetrated by fibrillar collagen or vice versa. The composite material may be applied on a solid support or reinforced with glass, plastics, cellulose, or metallic materials.

A method for the preparation of the composite material consists in dispersing of fibrillar collagen in a solution or a highly swollen dispersion of the synthetic hydrophilic polymer or copolymer in a lyotropic agent, e.g. in water diluted carboxylic acids, strongly acidified aqueous mixtures of ethanol and methanol, high-concentrated aqueous solutions of lyotropic salts, and high-concentrated aqueous solutions of urea or guanidinium chloride, at temperature not exceeding 37° C., and the subsequent removing of the lyotropic agent from the viscous dispersion at temperature not exceeding 37° C. using the known methods.

The crosslinking agent, e.g. trimethylolurea, formaldehyde, acetaldehyde, glutaraldehyde, starch dialdehyde, glyoxal, or Cr(III) salts, may be added in the course of preparation of the dispersion or after removal of the lyotropic agent.

3 Claims, No Drawings

COMPOSITE POLYMERIC MATERIAL FOR BIOLOGICAL AND MEDICAL APPLICATIONS AND THE METHOD FOR ITS PREPARATION

The invention relates to a composite polymeric material for biological and medical applications and to the method for preparation thereof.

The known method for manufacturing of substitutes of organs and tissues was based on composite materials, where one component was a three dimensionally crosslinked synthetic hydrophilic polymer of 2-hydroxyethyl methacrylate or a monomethacrylic ester of higher homologous glycols, and the other component was collagen. The above mentioned procedure consisted in the preparation of gel with opened pores of the size larger than 100 μm (micrometers) and in filling these pores, at least in part, with collagen in the course of polymerization or on completion of polymerization. The resulting composite material consisted of the insoluble spatial network of gel with the average pore size 100–400 μm and of collagen filling in the communicating pores and was modified in the way to attain a controlled resorption of the material after implantation into organism. Some biological properties of this composite material were published in M. Chvapil et all., J.Biomed.Mater.Res. 3, 315 (1969).

A disadvantage of this procedure is the final shape of product, which was obtained in the form of bulky blocks or similar spatial figures, e.g. a thick-walled tube. The shape of product can be modified only by difficult machining, as a rule in the frozen state when the material exhibits the necessary rigidity. In addition, the structure of this composite material is macroscopically rough, which fact leads in practice to a non-homogeneous intergrowing by tissues and to imperfect function of implanted prosthesis, e.g. to leakage of prostheses of tubular organs caused by an excessive porosity of their walls. The preparation of thin foils or coatings, e.g. on a textile base, is virtually impossible according to the above mentioned method. These difficulties, following from the used technological procedure, did not allow in particular application of these attractive materials in a larger practical scale beyond the frame of experiments with animals.

The above disadvantages are overcome by a composite polymeric material according to the invention, which consists of 1–99 wt. % of a hydrophilic polymer or copolymer based on methacrylic or acrylate, 1–99 wt. % of fibrillar collagen, 0–2.5 wt. % of a crosslinking agent (related to solids of both polymeric components), and, if it is desired, also of biologically active compounds and auxiliary materials, as plasticizers and fillers, and is prepared by dispersing the fibrillar collagen in a solution or in a highly swollen dispersion of the synthetic hydrophilic polymer or copolymer in a lyotropic agent and by the subsequent removal of the lyotropic agent.

The method for manufacturing of the composite material according to the invention consists in dispersing of fibrillar collagen in a solution or a highly swollen dispersion of the synthetic hydrophilic polymer or copolymer in a lyotropic agent, selected from the group comprising carboxylic acids diluted with water, strongly acidified aqueous mixtures of ethanol and methanol (pH 2–3), high-concentrated aqueous solutions of lyotropic salts, and high-concentrated aqueous solutions of urea or guanidinium chloride, under stirring at temperature below 37° C., and in the following removal of the solvent from the viscous dispersion at temperature not exceeding 37° C., thus forming a matrix of the synthetic polymer or copolymer penetrated by fibrillar collagen, or vice versa.

Another characteristic feature of the invention is, that a crosslinking agent, selected from the group comprising trimethylolurea, formaldehyde, acetaldehyde, glutaraldehyde, starch dialdehyde, glyoxal, and chromic salts, is added in the amount of 2.5 wt. % at utmost, related to the total amount of the synthetic polymer or copolymer and collagen, either during the preparation of dispersion or after removal of the lyotropic agent, and, if it is desired, also a biologically active component, filler, plasticizer, and the like, are added during the preparation of dispersion or after removal of the lyotropic agent.

The method according to the invention is characterized by (a) a separate preparation of the synthetic hydrophilic polymer or copolymer based on methacrylate or acrylate.

(b) dispersing the fibrillar collagen in a solution or a highly swollen dispersion of the synthetic polymer or copolymer mentioned sub a, using the solvent which has a high solvation effect on both polymeric components present and enables their mutual miscibility in the dispersed or dissolved form, (c) removal of the above mentioned solvent from the viscous dispersion mentioned sub b with formation of a matrix of the synthetic polymer or copolymer penetrated by fibrillar collagen, or vice versa, (d) the respective application of known crosslinking agents, which cause an intermolecular crosslinking of both polymeric components of the composition, while the said cross-linking agent may be added to the system either during preparation of the dispersion, as mentioned sub b, or first after removal of the solvent, as mentioned sub c, (e) the respective application of additives and/or auxiliary compounds, e.g. drugs or other biologically active compounds, plasticizers, fillers, or other additives, which can be added to the system in any of the mentioned steps, (f) the respective application of a suitable support or reinforcement, on which the viscous dispersion, mentioned sub b, can be applied by known methods and then the solvent can be removed as stated sub c, (g) the respective radiation sterilization of the final product encased in a suitable packing.

The described method overcomes the aforesaid shortcomings, substantially broadens the region of possible applications of the material, and renders some new qualitatively different morphologic and biologic properties to the material. Using the method according to the invention, a broad assortment of materials may be prepared for various biologic and medical purposes, while all these materials are marked by the more intimate contact of both participating polymeric components leading to a microscopically fine structure and to suitable biologic properties. All these new polymeric composite materials are also subjects of the invention. The preparation of the aforesaid polymers and copolymers, based on esters of methacrylic or acrylic acid, is sufficiently described in earlier patents, in particular in U.S. Pat. Nos. 3,575,946, 3,988,305, 4,076,921 and in Canadian Pat. No. 906 149. Suitable hydrophilic polymers according to the invention are, for example, poly(2-hydroxyethyl methacrylate), poly(2-hydroxyethyl acrylate), poly(5-hydroxy-3-oxapentyl methacrylate), poly(4-hydroxybutyl methacrylate), and poly(4-hydroxybutyl acrylate). As examples of suitable hydrophilic copolymers can be given, above all, copolymers of 2-hydroxyethyl methacrylate and/or 2-hydroxyethyl acrylate with the following monomers: butyl methacrylate, butyl acrylate, 2-ethoxyethyl methacrylate, 2-butoxyethyl acrylate, 4-hydroxybutyl methacrylate, and 4-hydroxybutyl acrylate. According to the invention, it is also possible to use the synthetic hydrophilic polymers or copolymers mentioned above in the mixture with microparticles of gels, as a rule, of the size about 0.5–10 μm. The gel microparticles act in the system as an active and physiologically harmless filler and the polymeric matrix prepared from such mixture exhibits a higher wet strength. These materials can be manufactured by the procedure according to the Czechoslovak Pat. No. 153 765 (Application 7234-71).

Glue stocks may be advantageously used as sources of collagen proteins according to the invention. The glue stock is transformed into a viscous material of known properties by alkaline or acidic swelling and by further processing commonly applied e.g. in the manufacturing of artificial sausage casings. The collagenic material preferentially used was freed of all ballast components by the known refining procedures, above all of foreign proteins and soluble or degraded fractions of collagen protein. This refined material consists in the main of insoluble fibrils and exhibits an extremely low antigenicity and a high stability to common proteolytic enzymes. It is therefore suitable for preparation of materials for implantation into living organism. For some purposes, e.g. for cultivation substrates for cell or tissue cultures, they may be used, according to the invention, also soluble types of fibrillar collagen, individually or in mixtures.

The known lyotropic agents are used in the preparation of dispersions of fibrillar collagen in the presence of the synthetic hydrophilic polymer or copolymer, namely the water-diluted carboxylic acids, e.g. acetic, malonic, or lactic acid, strongly acidified aqueous mixtures of methanol or ethanol (to pH 2–3), e.g. by acetic or hydrochloric acid, high-concentrated aqueous solutions of lyotropic salts, e.g. zinc(II) chloride, alkaline or ammonium thiocyanates, or magnesium perchlorate, high-concentrated aqueous solutions of urea or guanidinium chloride. The above mentioned lyotropic agents strongly swell or dissolve the fibrillar collagen and, in addition to it, dissolve also the aforesaid synthetic polymers or copolymers. The temperature should not exceed the limit 35°–37° C. during this procedure and also during other operations in the presence of the fibrillar collagen, otherwise an irreversible denaturation of collagen proteins takes place.

The fibrillar collagen is dispersed in the solution of synthetic polymer or copolymer, or vice versa, using known procedures, e.g. by vigorous stirring or by means of an ultrasonic disintegrator in the energy region where the perceptible breaking of polymer chains still does not set in. It is advantageous to use cooling during this process. According to the invention, the content of fibrillar collagen may be chosen within broad limits from 1 to 99 wt. %, related to the total solids of both polymeric components of the composite. The particular composition depends in practice from the real biological or medical application. Thus, for example, it was found, in the application of the composite containing 1 wt. % of fibrillar collagen in poly(2-hydroxyethyl methacrylate) of known properties as a cultivation base in vitro, that a mixed culture of myoblasts and fibroblasts became attached and continued to grow, while the synthetic polymer alone, though it was nontoxic, did not exhibit such properties. The upper boundary is virtually limited by the bonding ability of the used synthetic hydrophilic polymer or copolymer, which became apparent in most cases already from 1 wt. % of this component in composition. Obviously, a certain optimal ratio of both participating polymeric components and also a certain region of their mutual representations exist for any individual application, which fact enables to attain definite and defined biological properties of the resulting composite material.

The known methods may be used to remove the solvent from the viscous dispersion system, in particular:

(a) simple evaporation at temperatures not exceeding 37° C., as a rule at ambient temperature;
(b) evaporation in vacuum under the same temperature conditions as sub a;
(c) freeze sublimation in vacuum (lyophilization, freeze drying);
(d) preliminary extraction of the frozen dispersion in solid state with an agent which does not dissolve collagen but which is miscible with water in all proportions; e.g. with acetone or isopropyl alcohol, namely after the preliminary intercrosslinking of both polymeric components, e.g. by glutaraldehyde added to the dispersion, and the following evaporation of these agents according to the procedures given sub a or b;
(e) precipitation in water, while the addition of neutralization agent, e.g. aqueous ammonia, is necessary with dispersions having an acidic reaction, and drying of the swollen material by some of the aforesaid methods (a to d);
(f) precipitation in concentrated solutions of salts, e.g. chlorides or sulfates, most commonly of sodium chloride or ammonium sulfate, with acidic dispersions again in the presence of a neutralizing agent, most frequently of aqueous ammonia, the following washing of absorbed salts in water, and final drying as mentioned sub e.

The methods a to d are suitable for volatile or extractable solvents. The methods e and f are suited for all types of dispersions, as mentioned above, and are the preferred or only possible procedures of solvent removal with dispersions prepared by means of lyotropic salts. Each of the above given methods of solvent removal leads to some different results, in particular concerning the structure of material. The method a gives rise to nonporous films or layers, the method b leads to a roughly porous structure inside the layer and to a virtually nonporous upper skin (a sandwich type), the methods c and d render an elastic porous foam with communicating pores, and the methods e and f give to rise to fibrous materials with the structure of felt. The method of solvent removal is thus an important factor in the control of morphologic properties of the resulting composite materials.

To stabilize the given composite, particularly in the control of resorption rate of collagen fibrils after implanting the material into living environment of organism, it is possible to use, according to the invention, the known crosslinking agents for collagen. Most of these crosslinking agents, e.g. formaldehyde, glutaraldehyde, glyoxal, chromic salts, and the like, crosslink at the same time also the synthetic hydrophilic polymer or copolymer by the reaction with hydroxyl groups present in the side chains of these polymers. The mutual intermolecular crosslinking of both polymeric components of the composite system occurs parallelly and results in its enhanced chamical and, consequently, also biological stability. The above mentioned crosslinking agents, as a rule in the form of 0.05-2.5 wt. % aqueous solutions, may be added to the composite system either during the preparation of viscous dispersion or first after removal of the solvent in a separate step, while the degree of their cross-linking may be controlled by the concentration of crosslinking agent and the time of its action on the polymeric components of composition. The excess of crosslinking agents has to be removed from the final product, most often by washing in distilled water. In addition to the given crosslinking agents, it is possible to use, according to the invention, also other known crosslinking agents of collagen, for example, trimethylolurea, acetaldehyde, glutaraldehyde, or starch dialdehyde (oxistarch).

Also further compounds may be added, in addition to the above mentioned compounds, according to the invention, in any stage of preparation of the composite material, for example, drugs or other biologically active compounds, as wide-spectrum antibiotics with local effect (neomycin, gentamycin, and the like), or their suitable combinations, while these compounds may be present in the structure of composite in a free state and/or bound on the polymeric matrix through a chemical link or by ionic interactions. Further may be used compounds with anticoagulation or antiaggregation activity (e.g. heparin, Evans blue, etc.), compounds supporting healing and reparative processes of organism (e.g. local corticoids), compounds with an anticonceptive effect, and the like. In the external therapy, for example, for surfaces of wounds and burns (dressings, veils, temporary coatings), the biologically active compounds can be applied even outwardly, i.e. after placing the suitably chosen composite material on a wounded place, and the required level of medicine may be made up at any time because the hydrophilic character of composite materials according to the invention enables the permeation of medical compounds. Porosity of the porous materials allows a free passage even to high-molecular-weight compounds, particularly if they are in the form of aqueous solutions.

Further suitable additives may be external plasticizers, provided they are physiologically harmless, as for example, glycerol, polyoxyethylenes (particularly of mol. weight 400 and 600), glycerol mono and diacetate (a mixture of isomers), or their mixtures, namely in the application of the compositions in external therapy where flexibility and pliability are required.

The composite materials, prepared according to the invention, may be used as such and/or advantageously applied on a suitable support or other reinforcing material, e.g. tubular knitwork, woven net, made of medically harmless fibers [e.g. poly(ethylene terephthalate)], cultivation dishes made of glass or plastics which are used for cell and tissue cultures or for microbiological investigations. Further may be used nonwoven fabrics, suede, paper, regenerated cellulose (e.g. cellophane), or also supports from medically harmless synthetic polymers or copolymers and metals, e.g. in the form of foil, network, felt, and the like. The composite material may have various structures in this case (monolithic, micro and macroporous, sandwich, fibrous) and may be applied to these support in an arbitrary thickness.

Sterilization of these composite materials can be realized without damage, with respect to the presence of protein component, viz. collagen, practically only by radiation technique, either by gamma radiation ($Co^{60}$) or by beta rays using a linear accelerator of electrons. The reliable dose of radiation ranges between 2 and 2.5 Mrad in both cases and only minimum changes take place in the irradiated material, especially if it is in an anhydrous state. The sterilization is carried out in practice in a suitable protective casing, e.g. in a tightly sealed doubled polyethylene foil. Sterilization by means of oxirane derivatives is not recommended here, with respect to the possible chemical alterations of material and to toxic effects of residues and addition products of the sterilization agent.

The following examples illustrate the invention, but do not limit its scope in any possible performance and applications. As "collagen" has to be understood in all following examples the insoluble fibrillar preparation obtained by the EDTA method according to F. S. Steven, as described in "The Methodology of Conective Tissue Research", Chapter 4, pp. 19-27, editor D. A. Hall, Oxford 1976. Bovin hides were the starting raw material.

EXAMPLE 1

Poly(2-hydroxyethyl methacrylate) was prepared according to U.S. Pat. No. 3,575,946 by the solution polymerization of the corresponding monomer (10 wt. % of the monomer which contained 0.28 wt. % of the corresponding diester) in the cosolvent mixture ethanol-water (2:1 volume parts) at 80° C. for 9 hours under the inert atmosphere of $CO_2$, in the presence of dibenzoyl peroxide (0.25 wt. % related to the monomer) as the initiator of radical polymerization (conversion 78%), purified and isolated by reprecipitation into a large excess of distilled water (about tentimes larger volume), dried at laboratory temperature and ground in a laboratory mill to a fine powder—Characteristics: $\overline{M}_w = 8.7 \times 10^5$, $g' = 0.75$, $[\eta] = 1.26$ $dl.g^{-1}$. The stock solution of polymer (10 wt. % of solids) was prepared using a mixed solvent—1 volume part of glacial acetic acid (99%, analytical grade) and 2 vol. parts of distilled water.

Collagen was kept as a dispersion in 1% acetic acid containing 2 wt. % of solids in a refrigerator at 4° C. and the concentration of acetic acid was adjusted to 33 wt. % by addition of the calculated amount of glacial acetic acid under vigorous stirring in a kitchen blender shortly before the use. The calculated amount of the stock solution of poly(2-hydroxyethyl methacrylate) was added to the viscous dispersion of collagen to prepare the mixture of both polymeric components in the required weight proportion (1 to 99 wt. % of fibrillar colagen).

The corresponding composite dispersions were applied in a dust-free box on the inner surface of Petri dishes (60 mm diam.) made of plastics. Evaporation of the solvent at ambient temperature gave a thin film of composite which was additionally crosslinked for 24 hours by the 0.1% aqueous glutaraldehyde. After drying of setted films at ambient temperature, the Petri dishes were welded into a doubled polyethylene wrapper and sterilized with the dose 2.5 Mrad using a linear accelerator of electrons.

Fundamental biologic properties of the prepared composites were tested by the method of tissue cultures in vitro (a mixed primo culture of myoblasts and fibroblasts was used). It was proved in all cases that these materials were not cytotoxic, enabled fixation of cells on the support and their further growth, and enabled differentiation of cells, while the synthetic polymer alone, if applied under the same conditions, was not cytotoxic but did not allow the fixation of cells on the support and their further growth.

EXAMPLE 2

Poly(2-hydroxyethyl methacrylate) was prepared from the refined monomer containing 0.03 wt.% of ethylene dimethacrylate by the solution polymerization in 96% ethanol at the boiling temperature under reflux in an inert atmosphere of nitrogen. The initial polymerization mixture contained 85 vol. % of ethanol, 15 vol.% of monomer, and 0.2 wt. % of dibenzoyl peroxide (related to the monomer); after 10 hours of polymerization, the conversion to polymer of 85% was achieved. The polymer was isolated by reprecipitation in the excess of water and dried at temperature 40° C. in the vacuum of waterjet pump; characteristics: $\overline{M}_w = 2.3 \times 10^5$, $g' = 0.82$, $[\eta] = 0.89$ dl.g$^{-1}$. The further procedure was the same as in Example 1. Lower viscosity of the stock solution of poly(2-hydroxyethyl mathacrylate) proved advantageous in the preparation of dispersions of fibrillar collagen because it made the dispersing of collagen easier.

EXAMPLE 3

Poly(5-hydroxy-3-oxapentyl methacrylate) was prepared in a powdered form (0.5–10μm) by the precipitation polymerization of the corresponding monomer (containing 0.83 wt. % of the diester) in toluene, according to the procedure described in U.S. Pat. No. 3,988,305, and dissolved in aqueous ethanol (25 vol. %) to a viscous solution containing 10 wt.% of solids. The solution (2.4 weight parts) was blended in a kitchen blender for 2 minutes with the cooled collagen dispersion (8 weight parts) containing 2 wt. % of solids in aqueous ethanol (25 wt. %) and acidified by addition of hydrochloric acid (analytical grade) to pH 3. Glutaraldehyde (0.04 wt. parts) was added to the resulting viscous dispersion as the 25% water solution. The mixture was poured into a dish made of unplasticized poly(vinyl chloride), placed in a larger tight vessel, and all volatile components of the composite were removed at ambient temperature by means of a water-jet pump under formation of an elastic porous foam with the compact upper skin (sandwich structure) which contained 40 wt. % of fibrillar collagen. After thorough washing in distilled water followed by drying at ambient temperature in vacuum, the 5 mm thick layer of composite was obtained, which had the above described morphology and was suitable, for example, for covering of wounded surfaces (burns of 2nd and 3rd degree) after it was radiation sterilized by 2.5 Mrad dose in a polyethylene wrapper. Local medicines, e.g. aqueous solutions of antibiotics, may be applied outwardly.

EXAMPLE 4

The polymeric material containing 35 wt. % of gel microparticles was prepared by the procedure according to U.S. Pat. No. 4,076,921, i.e. by the precipitation polymerization of 2-hydroxyethyl methacrylate (10 wt. % of the monomer, which contained 0.28 wt. % of diester) in ethyl acetate (analytical grade). The following polymerization conditions were used: 0.3 wt, % of 2,2'-azobis(isobutyronitrile) related to the monomer as the initiator of radical polymerization, temperature 65° C., polymerization time 2.5 hours under an inert atmosphere of pure nitrogen, conversion to polymer 96.5%. The polymeric product was isolated by filtration, washed with a small amount of pure ethyl acetate, and dried in vacuum to a fine powder. The dispersion containing 10 wt. % of solids was prepared from this polymeric material in 1 M Mg(ClO$_4$)$_2$, where the soluble portion of the polymer formed a viscous solution with dispersed fine gel microparticles (1–1.5 μm) in a highly swollen state. This dispersion (1.5 wt. parts) was blended in a kitchen blender with the dispersion of fibrillar collagen (3 wt. % of solids) in 1 M Mg(ClO$_4$)$_2$, which was previously cooled to 4° C. The viscous dispersion was deaerated under reduced pressure and applied on a flat poly-(ethylene terephthalate) net, which was placed in a poly-(vinyl chloride) dish. The net with adhering dispersion was immersed into an excess of aqueous solution containing 25 wt. % of sodium chloride, where it coagulated and formed a fibrous precipitate which covered the net on both sides. The absorbed salts were removed by leaching in a flow of cold water and then extracted with distilled water. Glycerol (analytical grade, 5 wt. %) and neomycin (0.2 wt. %) were added into the last washing water, the material was allowed to soak in this bath for 6 hours at 4° C. (in a refrigerator), the bath was then decanted, and water was removed from the composite at ambient temperature by the vacuum of a water-jet pump. The pliable dressing material (a veil) was obtained, which was suitable, after the radiation sterilization, for covering of suppurative wounds or superficial wounds of skin because it had a high absorption capacity connected with the antimicrobial effect.

EXAMPLE 5

In the procedure according to Example 4, 1 M solution of sodium thicyanate in water was used as the solvent. Glycerol acetate (a mixture of 1,2- and 1,3-isomers) was used as an external plasticizer in the amount of 5 wt. %. Similar results were obtained as in Example 4.

EXAMPLE 6

The hydrophilic copolymer containing 70 wt. % of 2-hydroxyethyl methacrylate and 30 wt. % of butyl acrylate units was prepared using the procedure according to the Canadian Patent No. 906 149 by the solution polymerization in dimethylsulfoxide (DMSO) at the concentration of monomer mixture 10 wt. %, with 0.25 wt. % of dibenzoyl peroxide related to the sum of monomers. The polymerization was carried out at 80° C. for 7 hours under an inert atmosphere of $CO_2$ up to the conversion of 83%. The polymeric product was isolated by precipitation in water and purified by reprecipitation of the 5 wt. % solution in DMSO into water. The dried copolymer exhibited the softening temperature 19° C. and swelled in water up to the water content of 26 wt. %. The stock solution containing 10 wt. % of solids was prepared from the copolymer by dissolving in aqueous (33 wt. %) acetic acid. The dispersion containing 20 and 80 wt. % of fibrillar collagen were prepared by the procedure according to Example 1 and were further worked out, without addition of a crosslinking agent, by freeze drying (lyophilization) into the form of an elastic porous foam (thickness 3 mm)

suitable for covering of wounds on body surface, because they were sufficiently pliable at temperatures around 37° C. Sterilization of these products was performed by the radiation technique (the dose of gamma radiation from $Co^{60}$ was 2.2. Mrad). The material may be additionally combined with aqueous solutions of medicines, because the porosity of material enables their free permeation in spite of the reduced hydrophilicity of synthetic matrix. This covering mean is a sufficient barrier for outside bacteria and has therefore suitable properties for the application in external therapy.

EXAMPLE 7

A similar result as in Example 6 was attained with the copolymer containing 75 wt. % of 2-hydroxyethyl methacrylate and 25 wt. % of 2-ethoxyethyl methacrylate units, which was marked by some higher hydrophilicity, while about the same elastic properties in dry state were maintained.

EXAMPLE 8

The starting copolymer, prepared according to Example 6, was dissolved in 6 M aqueous solution of urea at the ambient temperature (18°–23° C.) to a viscous solution containing 10 wt. % of copolymer solids. The dispersion of collagen (10 wt. parts) in 6 M urea containing 3 wt. % of solids was mixed with the above solution under cooling to 4° C. and the resulting fluid was extruded through a circular nozzle into the coagulation bath consisting of the 20 wt. % aqueous solution of ammonium sulfate. The formed tube of composite of inner diameter 26 mm and outer diameter 30 mm was slided in a tubular poly(ethylene terephthalate) knitwork of diameter 32 mm, thoroughly extracted from ballast materials, radiation sterilized by a $Co^{60}$ source (the dose 2.2 Mrad), and used as an experimental prosthesis of esophagus in a dog.

EXAMPLE 9

According to the procedure described in Example 6, the dispersion of collagen was prepared in 6 M aqueous guanidinium chloride. The dispersion was extruded at low temperature (4°–10° C.) through a flat nozzle into a coagulation bath (water with 0.5 wt. % of aqueous ammonia added, 7° C.) and the formed fibrillar layer of swollen composite was washed by flowing cold water, dried at ambient temperature and a pressure 1.3 kPa, cut in pieces 10×10 cm, welded in a wrapping of polyethylene foil, and sterilized by a $Co^{60}$ source with the dose 2.2 Mrad. This composite material served as a carrier of medicines additionally applied by swelling of the coat in the solution of medicine (in this case in a mixture of chloramphenicole and colimycine 1000/80) and for covering a burn wound which was infected at wounding by environmental microorganisms. The additional dosage of the solution of medicine is possible directly through the temporary covering of composite material.

We claim:

1. A method for the preparation of a composite polymeric material for biological and medical applications, wherein fibrillar collagen is dispersed in a solution or a high-swollen dispersion of the synthetic hydrophilic polymer or copolymer in a lyotropic agent selected from the group comprising carboxylic acids diluted with water, strongly acidified aqueous mixtures of ethanol and methanol, high-concentrated aqueous solutions of lyotropic salts, and high-concentrated aqueous solutions of urea or guanidinium chloride, under stirring at temperature not exceeding 37° C. and then the lyotropic agent is removed from the viscous dispersion at temperature not exceeding 37° C.

2. The method according to claim 1, wherein a cross-linking agent selected from the group comprising trimethylolurea, formaldehyde, acetaldehyde, glutaraldehyde, starch dialdehyde, glyoxal, and chromium(III) salts, is added, during the preparation of dispersion or after the lyotropic agent has been removed, in the amount of 2.5 weight percent at utmost, related to the total amount of the synthetic polymer or copolymer and collagen.

3. The method according to claim 2, wherein a biologically active compound, and if it is desired, a filler and/or a plasticizer are added during the preparation of dispersion or after the lyotropic agent has been removed.

* * * * *